(12) United States Patent
Schouenborg et al.

(10) Patent No.: US 8,996,094 B2
(45) Date of Patent: Mar. 31, 2015

(54) METHOD AND SYSTEM FOR COMPENSATING A SELF-CAUSED DISPLACEMENT OF TISSUE

(75) Inventors: Jens O. Schouenborg, Lund (SE); Per Petersson, Lund (SE)

(73) Assignee: Neuronano AB, Karlshamn (SE)

( * ) Notice: Subject to any disclaimer, the term of this patent is extended or adjusted under 35 U.S.C. 154(b) by 732 days.

(21) Appl. No.: 12/159,518

(22) PCT Filed: Dec. 28, 2006

(86) PCT No.: PCT/SE2006/001506
§ 371 (c)(1),
(2), (4) Date: Jul. 11, 2008

(87) PCT Pub. No.: WO2007/075137
PCT Pub. Date: Jul. 5, 2007

(65) Prior Publication Data
US 2009/0020131 A1    Jan. 22, 2009

Related U.S. Application Data

(60) Provisional application No. 60/754,177, filed on Dec. 28, 2005.

(51) Int. Cl.
| | | |
|---|---|---|
| *A61B 10/02* | (2006.01) | |
| *A61B 19/00* | (2006.01) | |
| *A61G 13/02* | (2006.01) | |
| *A61G 13/06* | (2006.01) | |
| *A61B 5/0402* | (2006.01) | |
| *A61B 5/0488* | (2006.01) | |
| *A61B 5/113* | (2006.01) | |
| *A61B 17/00* | (2006.01) | |
| *A61N 5/10* | (2006.01) | |

(52) U.S. Cl.
CPC .............. *A61B 19/203* (2013.01); *A61B 5/0402* (2013.01); *A61B 5/0488* (2013.01); *A61B 5/113* (2013.01); *A61B 10/02* (2013.01); *A61B 2017/00699* (2013.01); *A61B 2017/00703* (2013.01); *A61G 13/02* (2013.01); *A61G 13/06* (2013.01); *A61N 2005/1097* (2013.01)
USPC ........... 600/426; 600/407; 600/410; 600/424; 600/425; 600/428

(58) Field of Classification Search
USPC .................. 600/407, 410, 415, 424–426, 428
See application file for complete search history.

(56) References Cited

U.S. PATENT DOCUMENTS 4,547,892 A * 10/1985 Richey et al. ...................... 378/8
6,357,066 B1 * 3/2002 Pierce ............................... 5/710
(Continued)

FOREIGN PATENT DOCUMENTS

WO    WO-2005/020819 A1    3/2005

*Primary Examiner* — Robert Chen
*Assistant Examiner* — Mark Remaly
(74) *Attorney, Agent, or Firm* — Dickstein Shapiro LLP (57) ABSTRACT

A system for compensating a neurally triggered or other self-caused displacement of a tissue of an animal including man comprises a base provided with a means for immobilizing the animal or body part thereof comprising the tissue, one or more displacement means in contact with the base, a means for sampling position data from a marker disposed in or in the proximity of the tissue, a means for sampling source activity data from one or more sources of displacement, microprocessor means for correlating position data and source activity data to generate a predictive correspondence, a means for controlling the one or more displacement means by source activity data based on the predictive correspondence. Also disclosed is a corresponding method and use.

31 Claims, 8 Drawing Sheets

(56) References Cited

U.S. PATENT DOCUMENTS

| | | | |
|---|---|---|---|
| 6,768,916 B2 * | 7/2004 | Heinold et al. | 600/415 |
| 2002/0091314 A1 * | 7/2002 | Schlossbauer et al. | 600/407 |
| 2004/0254439 A1 * | 12/2004 | Fowkes et al. | 600/407 |
| 2005/0059877 A1 * | 3/2005 | Falbo, Sr. | 600/407 |

* cited by examiner

METHOD AND SYSTEM FOR COMPENSATING A SELF-CAUSED DISPLACEMENT OF TISSUE

FIELD OF THE INVENTION

The present invention relates to a method for compensating a neurally triggered or other self-caused displacement of tissue of an animal including man and a corresponding system.

BACKGROUND OF THE INVENTION

In surgery, in particular micro-surgery, in the acquisition of biopsy samples, in medical imaging, in the recording of electrical activity from neurons and glia cells, and in therapeutic irradiation of tissue the geometric relationship between the affected tissue, at the one hand, and the surgical instrument, biopsy probe, imaging apparatus or radiation beam, on the other, should be stable. While a patient can be partially or wholly immobilized on a support to prevent him or her from moving during surgery etc., this does not prevent tissues under autonomous control from moving nor does it, for instance, hinder the patient from breathing or ventilating or from moving the eyes.

Methods for coping with such movements are known in the art. They comprise monitoring the changing position, i.e. the movement, of the tissue of interest in respect of an apparatus, such as an apparatus for imaging the tissue, or a radiation source for irradiating it or a device for interacting with the tissue, such as one for biopsy, etc. The apparatus or radiation source or device is displaced by motor means in a mirroring manner in respect of the moving tissue so as to keep its spatial relation to the tissue or its focus on the tissue constant over time. The motor means that effect the displacement are controlled by microprocessor means based on position data acquired by monitoring a movement of the tissue. The methods known in the art thus seek to trace the movement of a tissue as closely as possible and to use the position data acquired in this tracing to control the motor means as fast as possible via microprocessor means.

A problem with the methods known in the art is that they are only responsive to tissue movements, which are often difficult to predict. The time lag between the registration of a tissue movement and the thereon based counter measure controlled by the microprocessor and executed by the motor means taking effect often does not allow an acceptable compensation of such neurally triggered or other self-caused displacement of tissue.

Sources of involuntary body movements include heartbeats, respiration, peristaltic movements of the intestine, and muscular tremor. The movements of various organs and tissues are most often unrelated, that is, not concerted, and often are not uniform. They can interact in a complex manner making physiologically unrelated movements to add to each other or to compensate each other. Most often they cannot be predicted from a mere imaging of the tissue of interest.

OBJECTS OF THE INVENTION

It is an object of the invention to provide a method of the aforementioned kind which does not suffer of some or all of the drawbacks of the compensation methods known in the art.

It is another object of the invention to provide a system for carrying out the method.

Other objects of the invention will become apparent from the following short description of the invention, a number of preferred embodiments thereof illustrated in a drawing, and the appended claims.

SHORT DESCRIPTION OF THE INVENTION

According to the present invention is provided a method for compensating a neurally triggered or other self-caused displacement of a tissue of an animal including man, in which a compensating displacement of the tissue is initiated by an electric signal from the source of the neurally triggered or other self-caused displacement.

More specifically, according to the present invention, is provided a method for compensating a neurally triggered or other self-caused displacement of a tissue of an animal including man, comprised by a body part disposed, in a fixed relationship, on a base in contact with a displacement means, the method comprising: sampling position data from one or several index markers disposed in or in the proximity of the tissue; sampling source activity data from one or several sources of displacement; correlating the position data and the source activity data to generate a predictive correspondence; controlling the displacement means by the source activity data based on the predictive correspondence. In this application "displaced tissue" is a tissue, the self-caused displacement of which shall be compensated. A tissue "in proximity of" the displaced tissue is one that moves in concert with the displaced tissue. "Self-caused" signifies that the origin or cause of the displacement resides in the subject, in particular in the subject's nervous system. The method of the invention is capable of compensating a displacement of tissue in a macro range, that is, in the millimetre to centimetre range, but also in a micro range, that is, in the range of $<m^{-4}$-$m^{-6}$ and even less. In contrast to the methods known in the art that trace the movement of a tissue from position data obtained by imaging methods the method of the invention is based on the prediction of a movement from source activity data.

It is preferred for the method of the invention to comprise updating of the predictive correspondence in intervals or continuously.

In compensating a self-caused displacement by the method of the invention it is preferred to take into consideration tissue displacement, in the following called "artificial displacement", caused by the displacement means, in particular by their sudden acceleration and/or deceleration at the start or/and the end of a displacement-compensating movement. To prevent or minimize artificial displacement physical damping means such as, for instance, spring coil or rubber buffer means, can be arranged. Alternatively or in addition to the physical damping means software program means that control acceleration and/or deceleration of the displacement means can be provided.

According to a first preferred aspect of the invention, the displacement of the base is linear.

According to a second preferred aspect of the invention the displacement of the base is in a plane.

According to a third preferred aspect of the invention the displacement of the base is in three dimensions.

According to a fourth preferred aspect the base comprises a means for holding an animal or a person or a body part thereof in a fixed relationship to the base. The holding means is preferably disposed on the upper face of the base; it is mounted at the base or integral with the base. The holding means can be a frame provided with clutches, ribbons, etc. in which the person or animal or body part is placed and to which it is fixed. The frame can be arranged displaceable on the base to hold the animal or patient or body part thereof in a desired position; for instance the frame can be fixed at the base by a restricted number of screws, such as from one to six screws, in a corresponding number of threaded bores of an array of bores arranged in the top face of the base. The frame can also be clamped to the top face of the base in a selected position. The choice of the means for fixation or immobilization of the animal or patient or body part thereof is not critical. Any releaseable fixation means suited for this purpose can be used.

According to a further preferred aspect of the invention the displacement means is selected from electrical motor means, solenoid means, and hydraulic means. The combined use of displacement means of different kind is within the ambit of the invention, as is the use of two displacement means for displacement of the base in one direction: a first means for coarse displacement and a second means for fine displacement. Advantageously the means for fine displacement may be used for displacement correction based on feedback from a position sensor.

If the displaced tissue is mucosal tissue, in particular skin tissue, or a tissue adjacent to the mucosa or the skin, it is preferred for an index marker to be disposed on the mucosa or the skin. The marker can be, for instance an ink mark applied to the skin. The position of the marker can be ascertained photographically, such as by video, in particular high speed video, the position data thus being video data. If the displacement is three-dimensional it is preferred to monitor the displacement of a marker disposed on the mucosa, in particular in the skin, from two or more angles. Light emitting diodes (LED) or other miniature light sources disposed on the mucosa, in particular on the skin, can also be used as index markers. Alternatively the position of a marker can be followed by laser Doppler shift detecting equipment.

If the displaced tissue is one located at such a distance from the mucosa or the skin that its displacement cannot easily be followed by observation of a marker displaced on the mucosa or skin, respectively, the marker is one implanted in the displaced tissue or in a tissue adjacent to the displaced tissue. In such case the marker is one that can be detected by a suitable tissue-penetrating imaging technique such as ultrasound, magnetic resonance or X-ray. An implanted marker is preferably metallic or comprises a metal. Alternatively the movement of a marker implanted in deep tissue can be followed by surgically implanted fibre optics. It is also within the ambit of the invention to use, as an implanted marker, an anatomic structure on or in the displaced tissue or on or in a tissue adjacent to the displaced tissue the position of which can be followed by one of the aforementioned methods. It is also preferred for an implanted marker to be resorbable by the tissue into which it has been implanted. A suitable material for a resorbable marker is, for instance, a polyester, such as poly(lactide), poly(glycolide), poly(lactide, glycolide), the matrix thereof optionally containing a radiation opaque biocompatible and resorbable material such as calcium carbonate and calcium phosphate. Resorbable radiopaque markers are disclosed in US 2005/0036945 and U.S. Pat. No. 6,862, 470 B2, which are incorporated herein by reference.

Preferred source activity data comprise electromyographic (EMG) data from skeletal muscle, such as data of respiratory muscles (Resp-EMG) and electrocardiogram (ECG) data.

According to a second preferred aspect of the invention the drive means is capable of planar displacement of the base.

According to a third preferred aspect of the invention the drive means is capable of three-dimensional displacement of the base.

According to another preferred aspect of the invention a drive means for linear displacement of the base can comprise two or more drive sub-means acting in the same direction and/or in an opposite direction. The combination of a drive sub-means for coarse displacement and a drive sub-means for fine displacement, such as a drive means for displacement in the centimetre range and another in the millimetre range or one in the millimetre range and another in the micrometer range, is preferred. According to a preferred embodiment a drive means for fine displacement is disposed separate of the drive means for course displacement, preferably as close as possible to the body part in which the tissue of interest is located. In particular preferred is a control of frame displacement in respect of the base by a drive means for fine control. A drive means for fine control can comprise an electrical motor or a hydraulic cylinder. In an embodiment of the invention in which a movement of the brain stem, such as a movement caused by the heart beat or by breathing, shall be compensated the drive means for fine control are arranged to work on the frame or the skull of a patient or animal.

The base of the invention is preferably substantially flat and designed to be displaced in a plane corresponding about to a horizontal face thereof; in a preferred embodiment the base rests on one or more flat faces of a support via an interposed array of spheres. If the support comprises two or more faces they are disposed in one or more parallel planes. The frictional resistance to the displacement of the base should be kept as low as possible. Another preferred arrangement of the base on the support, in which the frictional resistance to displacement of the base is minimized, is via a cushion of air flow.

DESCRIPTION OF THE FIGURES

The invention will now be explained by reference to a number of preferred embodiments illustrated in a drawing, in which.

DESCRIPTION OF PREFERRED EMBODIMENTS

Figure 1:
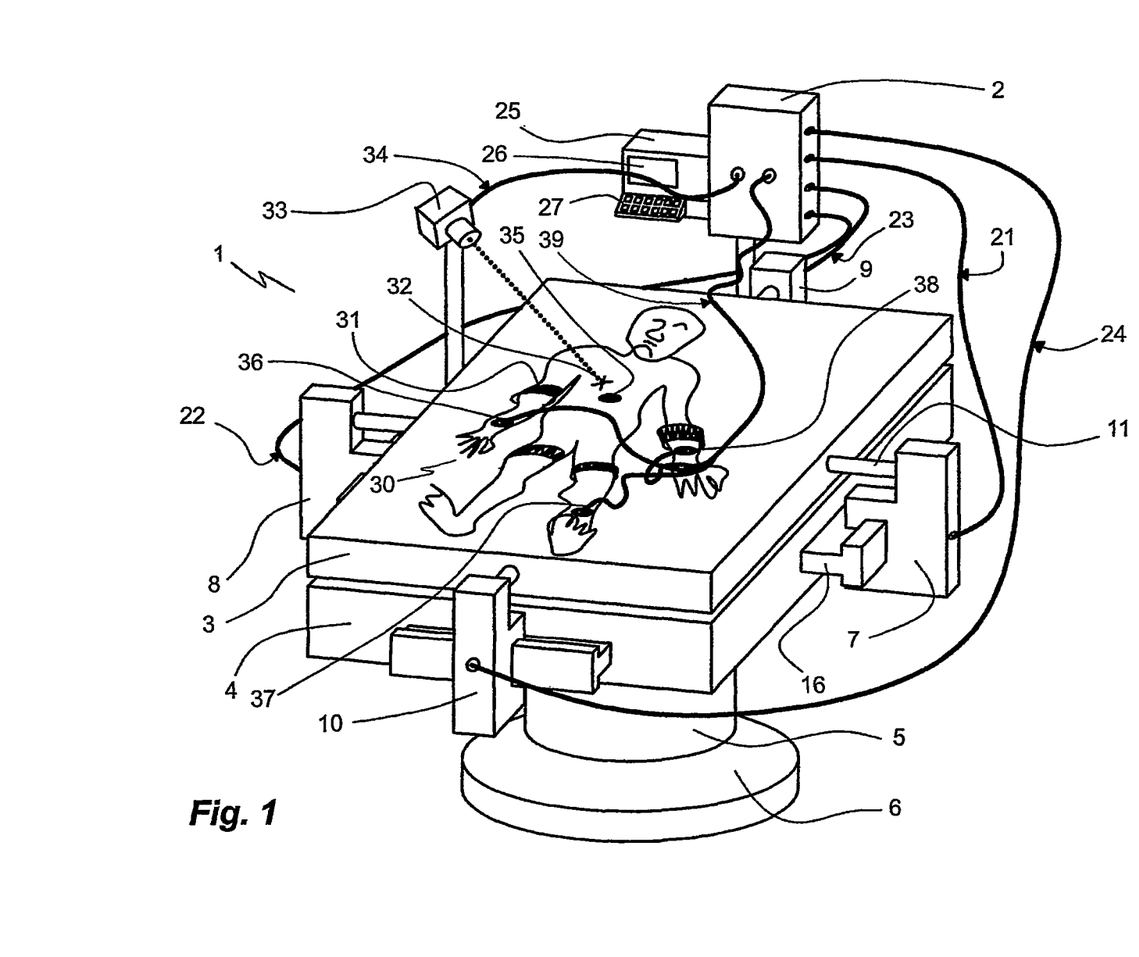
FIG. 1 is a first embodiment of a positioning system of the invention, in a perspective view.
Figure 2:
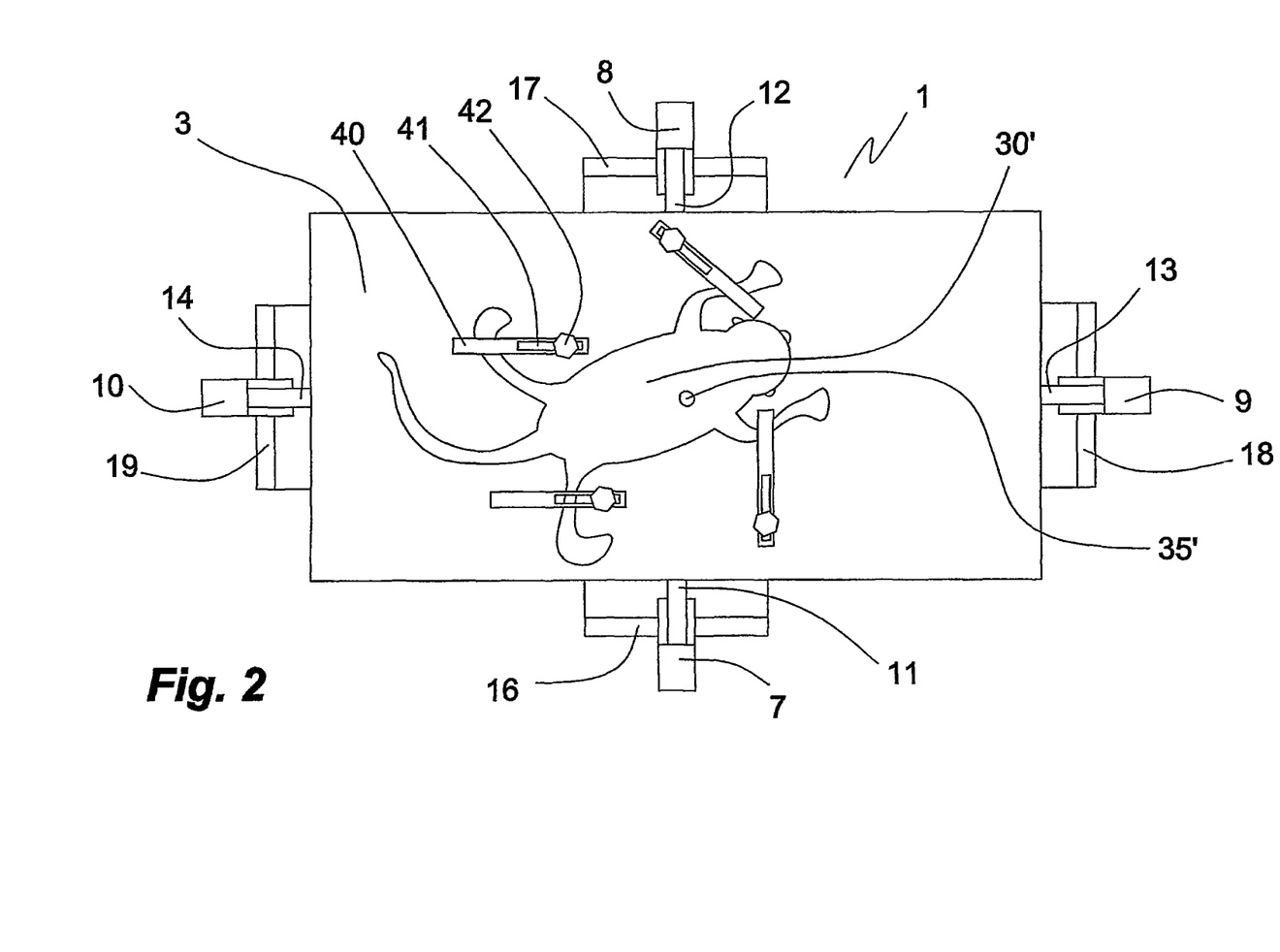
FIG. 2 is a patient or animal support table of the system of FIG. 1, in a top view and with an animal disposed on the table in a fixed relationship.
Figure 2A:
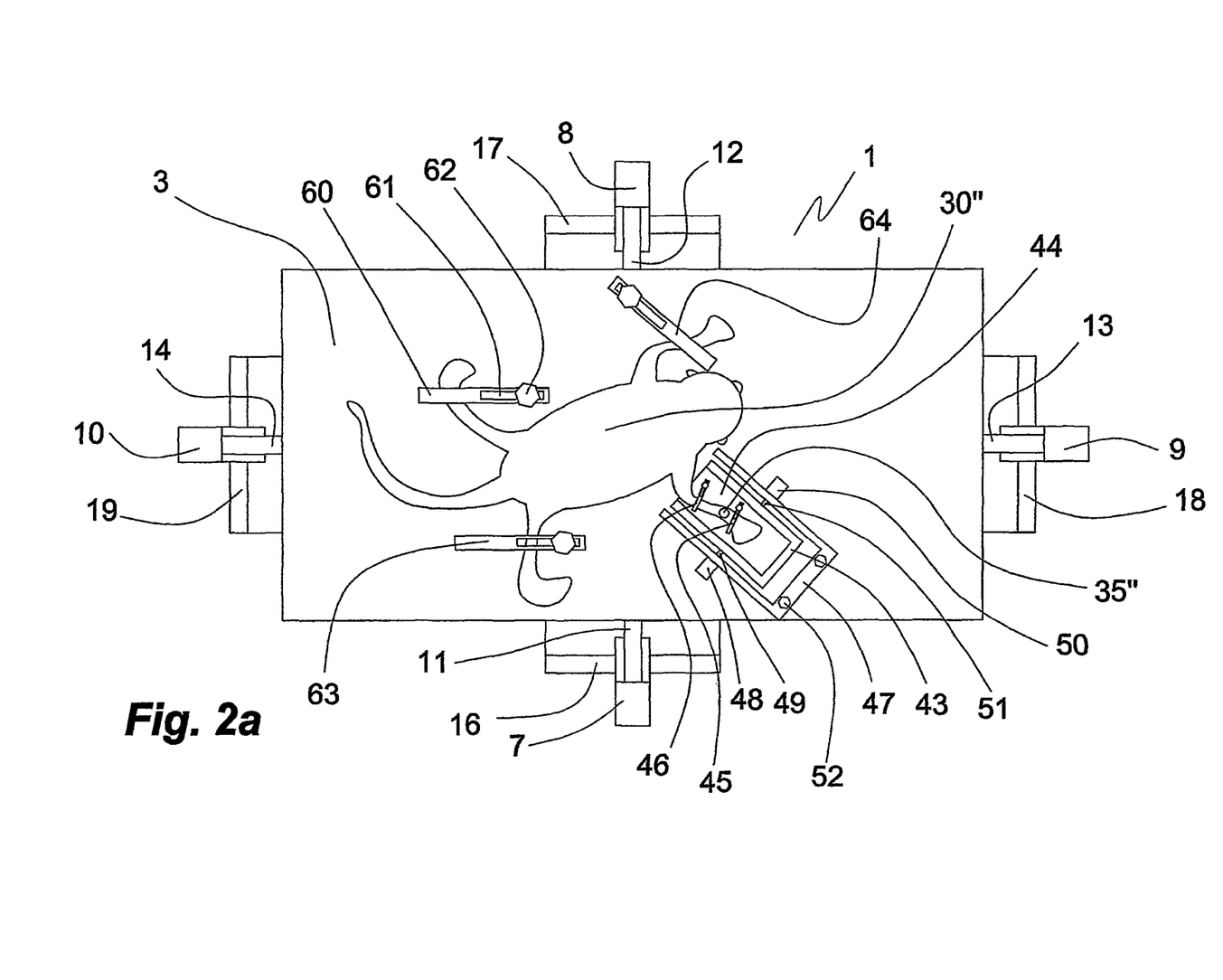
FIG. 2a is a patient or animal support table of the system of FIG. 1, in a top view and with an animal disposed on the table in a fixed relationship in respect to a frame mounted on the table.
Figure 3:
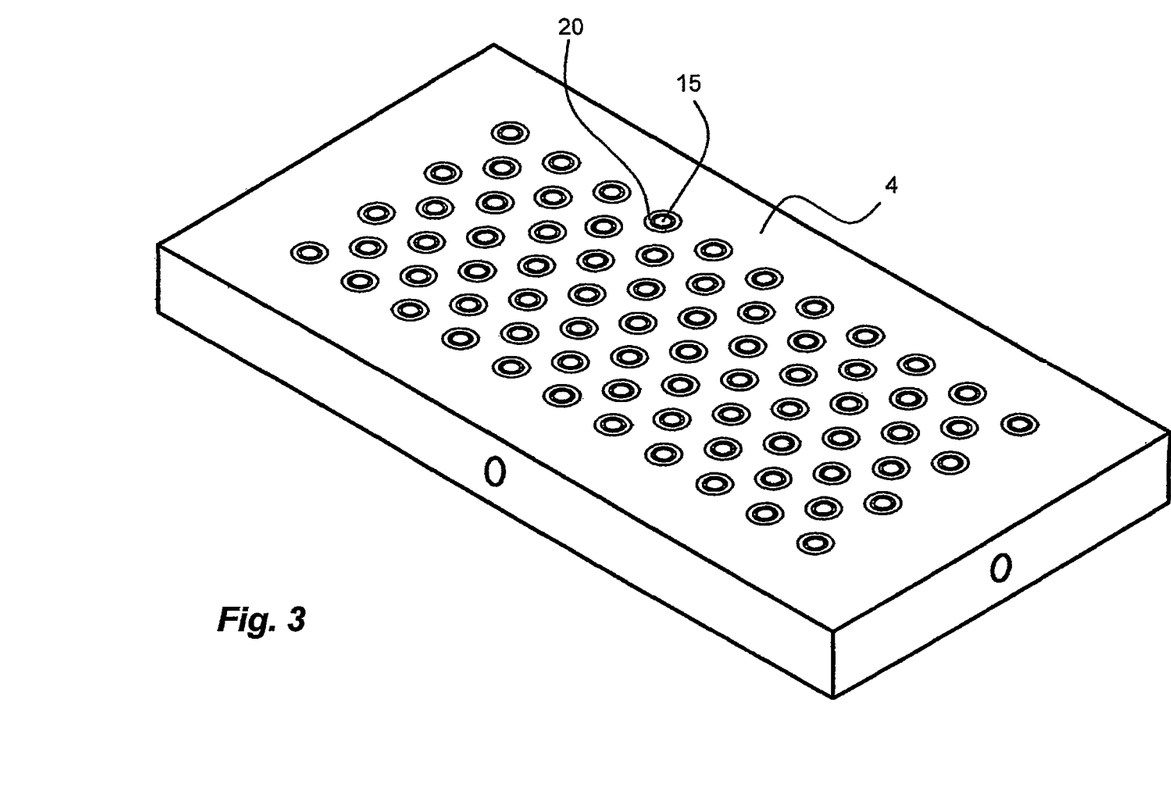
FIG. 3 is a support of the base of the patient or animal support table of FIG. 2, in the view of FIG. 1.

A patient 30 rests in a recumbent position on a patient or animal base 3 of a positioning table 1 of a first embodiment of the positioning system of the invention (FIG. 1; reference is also made to FIGS. 2, 2a and 3). The base 3 has the general form of a rectangular plate. The patient is immobilized on the rigid base 3 by means of a plurality of straps 31 (FIG. 1). The positioning system includes a displacement control unit 2 comprising an operator interface 25. The base 3 is displaceable in the horizontal plane defined by its parallel flat lower face, which glides on the parallel flat upper face of a rigid support 4 mirroring the lower face of the base 3 and of corresponding form, carrying an array of spheres 15 (FIG. 3) secured in their bearings by locking rings 20. In FIG. 1 the gap between the base 3 and the support 4 is shown somewhat exaggerated. The base 3 can be displaced horizontally by co-operating pairs 11, 12; 13, 14 of pistons controlled by pneumatic cylinders disposed in cylinder housings 7, 8, 9, 10. The pistons 11, 12; 13, 14 of each pair are centrally fixed to opposite side walls of the base 3. The cylinder housings 7, 8; 9, 10 run on rails 16, 17, 18, 19, respectively, which are centrally mounted to opposite side walls of the support 4 and extend in a horizontal direction. The support 4 is centrally supported by a column 5 comprising a circular foot 6. Fluid is provided to the pneumatic cylinders in the housings 7, 8, 9, 10 from by means of electric pumps in the housings (not shown) under control by the displacement control unit 2 via cables 21, 22, 23, 24. The control unit 2 comprises a microprocessor and displacement control software stored in a memory. Commands to the microprocessor are entered by an operator via the keyboard 27 of the interface 25. Operation parameters and other information are displayed on the monitor 26.

The patient 30 has been elected for surgery in a tissue 35 of the chest, which is influenced by the autonomous movement of the heart and the movement of respiratory muscles. To prevent the effect of non-autonomous respiration events the patient has been put under general anaesthesia. The movement of the tissue 35 is monitored by a video camera 33 focussed on a marker 32 affixed to the skin at a close distance from the tissue 35. Image data from the camera 33 is transferred to the central unit 2 by means of a video cable 34. Instead of the video camera 33 a laser Doppler probe can be used, for instance. For determination of the marker's 33 location in space required in the compensation of a movement of the tissue 35 in three dimensions images from two or more video cameras will have to be provided. ECG electrodes 36, 37, 38 are attached to the underarms and the left leg of the patient 30 to monitor the patient's heart activity; their leads are connected to the control unit 2 via a bus 39; alternatively the electrodes 36, 37, 38 can be attached to the breast of the patient. However, a single electrode placed on the breast of a patient or animal is usually sufficient to record the onset of heart activity. To obtain fuller information additional ECG electrodes can be attached to appropriate sites and connected to the control unit 2; for reasons of clarity this is however not shown in the figure.

In FIG. 2 the patient or animal base 3 of the positioning table 1 of FIG. 1 is shown with an animal 30' disposed on it. The animals 30' legs are fastened to the base 3 by four clamps 40 mounted to threaded bores in the base 3 by bolts 42 extending through slits 41 in the clamps 40. This arrangement immobilizes the animal 30' on the base 3. By the design of the clamps and the provision of an array of bores (not shown) for mounting the screws 42 the animal 30' "can be immobilized on the base 3 in a desired position. The tissue 35' is prevented from neurally triggered or other self-caused displacement in the plane of the base 3 by hydraulic cylinders 9, 10, 11, 12, as explained in respect of FIG. 1.

In FIG. 2A the patient or animal base 3 of the positioning table 1 of FIG. 1 is shown with an animal 30" disposed on it. Three of the animal's 30' legs are fastened to the base 3 by clamps 60, 63, 64 provided with slits 61 through which bolts 62 extend. The bolts 62 are mounted in selected bores of an array of treaded bores (not shown) arranged in the top face of the base 3. The fourth leg of the animal 30" is fastened by clamps 45, 46 to the bottom plate 44 of a U-formed inner frame 43. The inner frame 43 is glidingly disposed on the base 3 and can be displaced in opposite directions perpendicular to its legs by means of hydraulic cylinders 48, 50 mounted at the legs of a U-formed outer frame 47. The outer frame 47 is mounted to the base by bolts 52 and encloses the inner frame 43, on which the piston rods 49, 51 of the hydraulic cylinders 48, 50 are working. The hydraulic cylinders 49, 50 are designed for fine-tuned displacement of the inner frame 43 in co-operation with the course displacement of the base 3 provided by the hydraulic cylinders 7, 8, 9, 10. This protects the tissue 44 of interest in the clamped leg from neurally triggered or other self-caused displacement.

Figure 4:
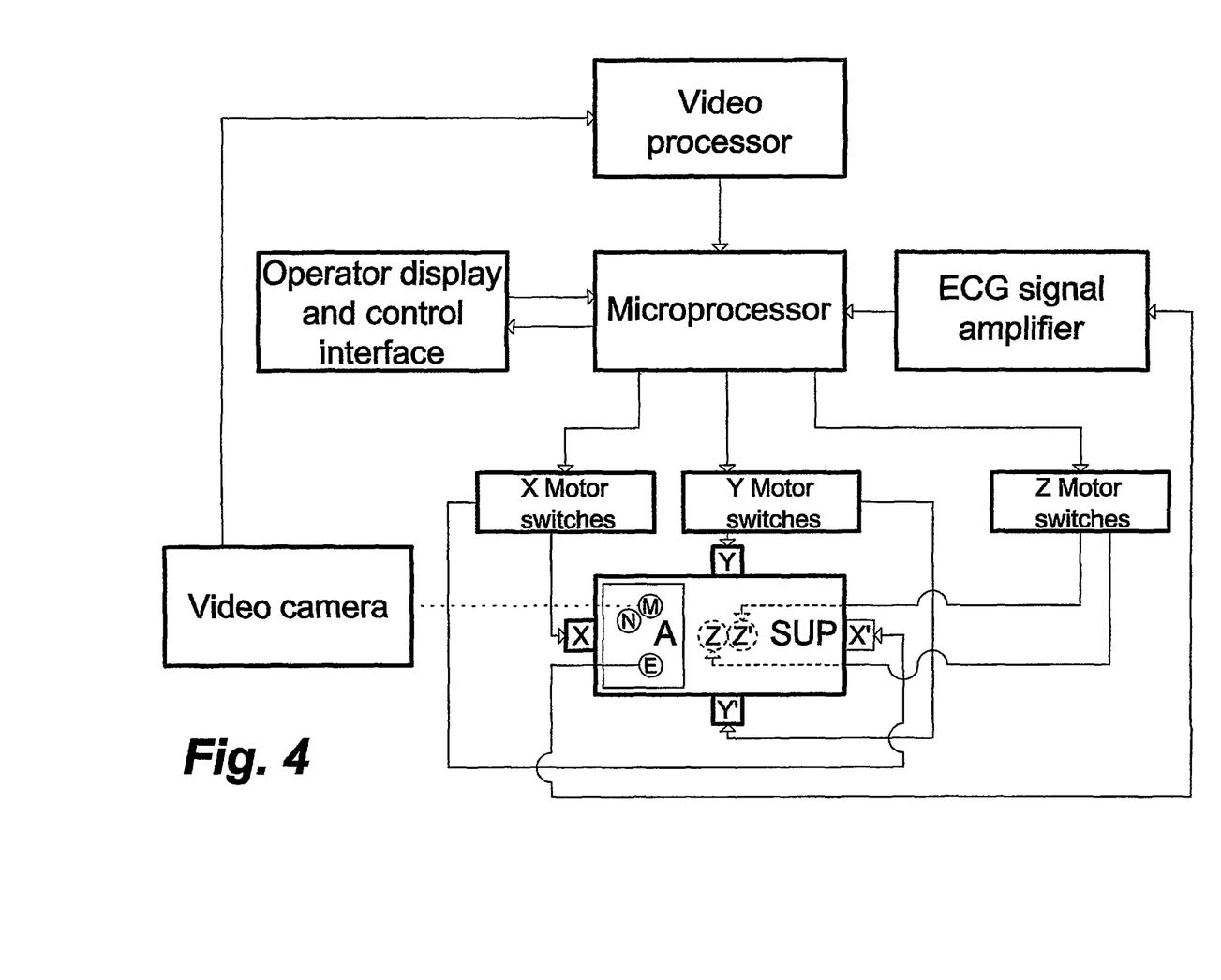
FIG. 4 is a block diagram of another embodiment of the system of the invention.
Figure 5:
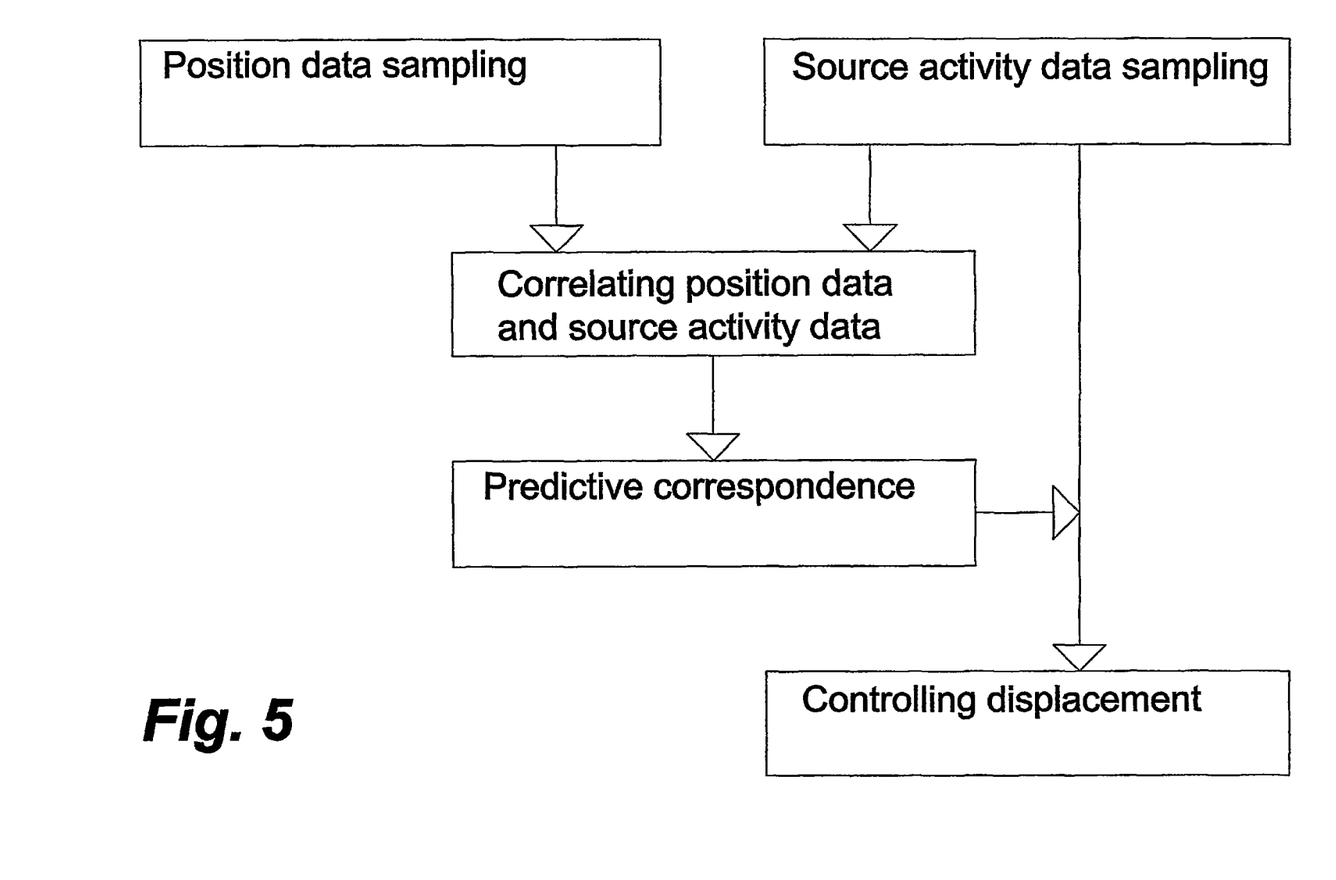
FIG. 5 is block diagram of an embodiment of the method of the invention.

Reference is now made to FIGS. 4 and 5. The block diagram of FIG. 4 is a schematic rendering of an embodiment of the displacement compensation system of the invention. A mammal A is immobilized on a horizontal support SUP. A tissue N of the mammal shall be prevented from moving during surgery, biopsy, irradiation, etc.; due to the vicinity of the tissue N to a major artery, the tissue N is affected by the expansion and contraction of the artery during a cardiac cycle, and thus displaced. The movement of the tissue N is monitored by a video camera focussed on a marker M disposed on the skin in close proximity of the tissue N. The video signal is sent to a video processor in which the image is analyzed to determine and to update the coordinates of the marker M, which are stored in the memory of a microprocessor. Additionally and independently thereof the microprocessor receives amplified ECG signal data from a set of electrodes E (only one shown) mounted on the mammal A. The signal data are analyzed in an ECG analyzing unit integrated in the microprocessor to obtain an electrocardiogram. The electrocardiogram is searched by dedicated software/hardware for a selected event, such as a Q wave, that precedes and thus predicts the contraction of the left ventricle. Identification of the Q wave triggers the microprocessor to instruct X and/or Y motor switches to start one in a pair of motor means X, X' and Y, Y' working on the support SUP to effect an appropriate displacement thereof in the x,y-plane. The distance and direction of displacement is based on an earlier displacement of the marker M recorded by video, so as to compensate for the displacement over the time interval during which it occurs. The motor means X, X'; Y, Y' can, for instance, be electric motors but a combination of electric fluid pumping means and pistons in pneumatic cylinders that can be displaced by the fluid is preferred. The paired motor means work in opposite directions. If the motor means comprise electric motors, in particular DC stepping motors, one motor does, in principle, suffice for linear displacement in both directions since its polarity can be easily changed. The need for precise and, most important, fast displacement however suggests the use of paired motor means. If necessary, displacement in a z-direction perpendicular to the x,y-plane (in a vertical direction) can be effected by activation of Z, Z' motor means via Z motor switches. The tissue N is displaced with the support SUP. Thereby the tissue N keeps its position in space in relation to, for instance, a surgical instrument or a radiation source. The ECG data contain information predictive of the onset of systole. The source of contraction of the heart muscle is the electrical activity of the conduction system of the heart. The ECG data, therefore, may be termed "source activity data". The microprocessor correlates the position data (video data) with the amplified and analyzed source activity data (ECG data) to provide a predictive correspondence. The predictive correspondence between position data and source activity data is used to control the motor means X, X'; Y, Y', Z, Z' that effect the displacement of the support SUP. The position data are continuously updated by video monitoring of the marker M; the updated data are compared with position data stored in the memory of the microprocessor. If a difference between an updated data and a stored data is recognized the updated data is used to correct the correlation between position data and source activity data and, hence, predictive correspondence. Thereby a change in, for instance, minute volume or a breathing interference can be coped with. The software stored in the microprocessor comprises an algorithm that controls the acceleration and deceleration of the motor means to minimize retardation effects during displacement on the tissue N caused by the inertia of adjacent soft tissues.

Alternatively, a contraction of respiratory musculature that risks displacing the tissue N can be predicted by monitoring the electric activity of the relevant nerve(s); suitable implantable electrodes for that purpose are known in the art. Intramuscular electromyographic (EMG) recordings of respiratory movements can be made from muscle groups contracting in the inspiration phase, in particular from rostral parasternal intercostal muscles, the sternocleidomastoid muscle and diaphragmal muscles, and from abdominal muscle groups contracting in the expiration phase, in particular from m. rectus abdominis, m. obliqus internus abdominis, m. obliqus externus abdominis, m. transversus abdominis, and from intercostal muscles, in particular m. triangularis sterni. A method of providing EMG recordings from muscles involved in respiration suitable for use in the present invention is disclosed in Grandevia et al. J Physiol 573:263-275, 2006, which is incorporated herein by reference. While surface recordings from some of these muscles may also be used in the method of the invention their signal to noise level is much lower than from intramuscular recordings and thus not preferred.

In a normal as well as in an abnormal neurological state of a patient or animal tremor in skeletal muscles may occur. Tremor is a periodical contraction and relaxation of skeletal muscles, and may be transmitted to a tissue that shall be prevented from displacement. Physiological tremor of a frequency of 8-10 Hz occurs in physically active or inactive healthy persons. Damage of certain regions of the nervous system, such as basic ganglia and the cerebellum, may increase tremor considerably both in a physically active state of the person or animal and at rest. Tremor caused by such damage can occur at frequencies outside the frequency range of physiological tremor. To compensate for tremor, EMG is recorded in an affected skeletal muscle, preferably via one or more electrodes inserted intramuscularly. Such electrodes are commercially available and in clinical use.

Movements of internal organs, for example the stomach, the intestine, and the bladder, often occur periodically. In such case the electrical activity of such muscle, most often smooth muscle, can be recorded by inserting one or more electrodes into the muscle or disposing them in the vicinity of the muscle. Electrodes for use in skeletal muscle or for use in the nervous system can be used for recordings from smooth muscle.

Signals in the nervous system that trigger the activity of a muscle precede that activity by several milliseconds, sometimes by up to 30-100 ms. In certain situations it is advantageous to record such signals from the nervous system instead of or in addition to signals emanating from the respective muscle. Recordings from the nervous system can be made by means of an electrode implanted in a tremor-causing motor centre or from motor nerves. Suitable electrodes are commercially available; they can comprise or consist of a thin wire of platinum, gold, stainless steel or a suitable alloy but also of, for instance, an electrically conducting polymer. The electrodes can be implanted in the nervous system by surgery or by percutaneous insertion into peripheral nerves.

Figure 6:
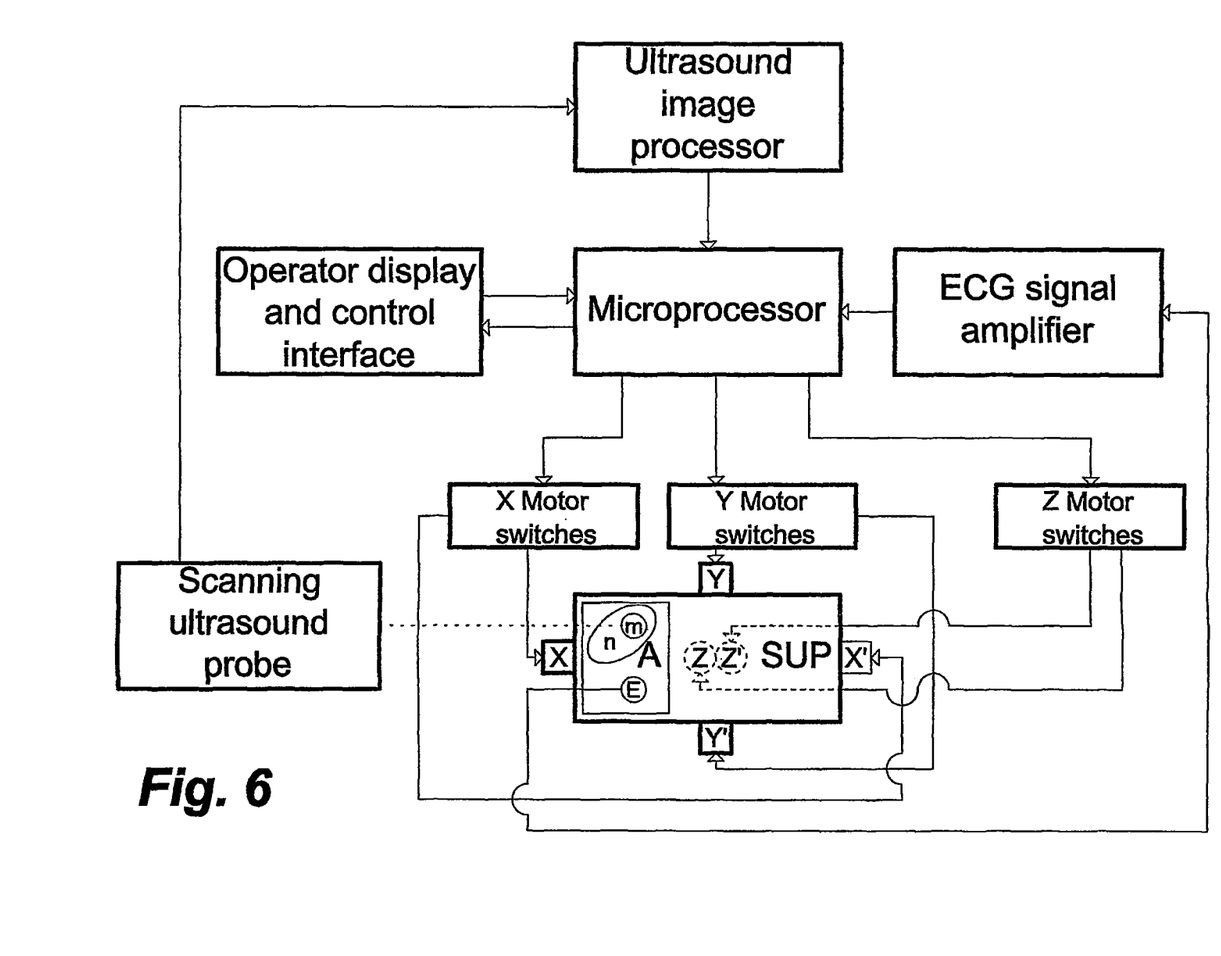
FIG. 6 is block diagram of a third embodiment of the system of the invention

FIG. 6 is a block diagram of another embodiment of the system of the invention. Only elements differing from those of the system illustrated in FIG. 4 will be described. The movement of a deep-level tissue m of a mammal a, which is immobilized on the support SUP, is not accessible to direct or indirect video monitoring of a marker on the skin surface bordering to an adjacent tissue. A marker m is implanted in the tissue n. The position of the marker m is monitored by sweeping the tissue n with an ultrasound probe. The reflected ultrasound signal is fed to an ultrasound image processor, in which it is transformed to a series of digitized two-dimensional images. A three-dimensional image, which allows the exact location of the marker m, is created from the series of two-dimensional images from different sight lines. The marker m position data thus obtained are correlated with ECG source activity data in the microprocessor as described above for marker M position data obtained by video.

Figure 7:
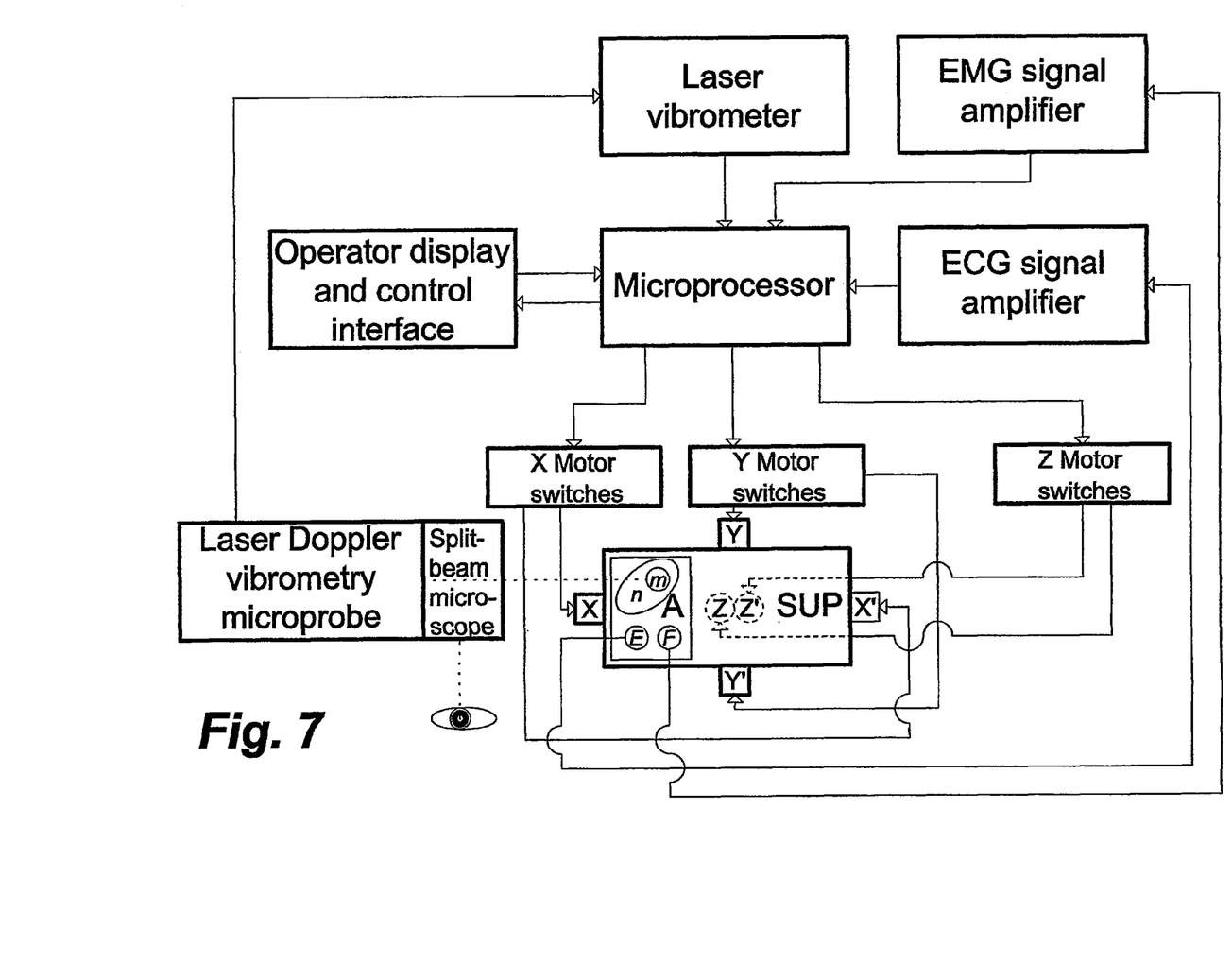
FIG. 7 is a block diagram of a fourth embodiment of the system of the invention

The embodiment of the system of the invention shown in FIG. 7 is an example of an arrangement for compensating micro-scale displacements of a tissue n in which a marker m is implanted. For an explanation of elements already present in FIGS. 4 and/or 6, reference is made to these figures. The tissue n is visualized under magnification in a microscope. Position data of a marker m in the tissue n are sampled by a laser Doppler vibrometry microprobe mounted to a split-beam microscope. The signal from the laser Doppler probe is demodulated in a laser vibrometer from which position data are transferred to a central microprocessor unit. Source activity data sampled by ECG and respiratory EMG probes (E; F) are transferred to ECG and EMG signal amplifiers, respectively. The amplified signals are fed to the central microprocessor unit, where they are analyzed and correlated with marker m position data as described above for marker M position data obtained by video. Pairs of motors X, X'; Y, Y'; Z, Z' are actuated via respective motor switches to displace the support SUP on which the tissue n is immobilized in a manner so as to compensate for its displacement caused by the activity of the heart and musculature involved in inspiration.

An important property of a software for analyzing in-data from sensors and video to control compensatory displacement of the tissue that shall be kept from moving in one or two dimensions or in three-dimensional space is that the in-data must be treated in a very short time, such as 1 millisecond or less, so that the time difference between the last received in-data used in an instruction to a displacement means, such as a hydraulic means or an electrical motor, and the corresponding instruction is very short, such as one or two milliseconds and even less. A compensatory displacement that can be relied on by the operator will usually have to be calibrated in advance. A typical calibration will take about 10 min but may be as short as one min. By the calibration the operator does establish a relation between the source signals and the movement of the tissue of interest as determined, for instance, by video or ultrasound. Then a compensatory displacement of the tissue by one or more actuators based on the foregoing calibration is optimized by the operator and/or the software. The operator can follow the optimization process on a screen or by means of printout data or in any other adequate manner. In a second step the optimized compensatory displacement data then is stored in the microprocessor memory. The instructions by the software to the one or more actuators are a mirror image of a tissue movement predicted by live in-data and/or stored in-data that may have been analyzed and modified or not.

This two-step calibration is followed by determination of criteria for reliable detection of the onset of respiration/inspiration activity and ventricular/atrial heart activity. The reliability of such determination increases with the length of a sampling period during which sampling position data and source activity data are sampled and stored in the memory. From these data a threshold value or a threshold profile for a source activity data on which a compensatory displacement is based is calculated. The threshold value or the threshold profile then is monitored by a source activity data sensor. Compensatory displacement instructions by the microprocessor to an actuator are triggered by the threshold value being recorded or the threshold profile being identified by the microprocessor. Since there may be a drift of the movement of the tissue of interest over time it is important to monitor for a drift and, if detected, compensate for the drift by the software in the microprocessor re-setting the threshold value or modifying the threshold profile. It is also important to monitor a potential drift of the source activity data that affects the threshold value or the threshold profile value, and to compensate for such drift. An error signal, that is, a signal of a deviation from the predicted displacement pattern of the tissue of interest recorded by the video or other position data monitoring means, is used to update a predicted tissue movement pattern. To obtain a gradual improvement of the predicted tissue movement pattern, and to thereby avoid large oscillations in the pattern, updating of the predicted movement pattern can occur in small steps, such as by 5% of the error signal or less for each updating cycle. The correction of the predicted tissue movement pattern is implemented by the software in the following compensation cycle. The percentage of the error signal used in such updating can be set by the operator or be integrated in the software. The updating of the predicted movement pattern can also be implemented by means of a Kalman filter, which scales the weight of the feedback signal, i.e. the signal of a deviation from the predicted displacement pattern of the tissue of interest recorded by video or other position data monitoring means, in relation to an earlier determined model for proactive correction. In the event of an unexpected large movement of a tissue of interest the actuator displacement can be limited to consecutive fractions of the time interval during which the unexpected movement occurs. In the case of a noticeable variation in a source activity amplitude data this enables the proactive correction to be updated stepwise and thus to use source activity data for predicting the amplitude of a periodical movement. The use of source activity amplitude data allows a corrective compensatory displacement by an actuator to be scaled in proportion. In an embodiment of the apparatus of the invention using separate actuators for fine and coarse displacement in one or more directions it is necessary to correspondingly update the proactive correction at both the fine and the coarse displacement level.

The position of tissue of interest can also be measured with commercially available probes. One example is a fibre optic probe that detects light reflected back from a marker disposed on a tissue or from a tissue (MTI-2100 Fotonic Sensor, MTI instruments, Inc.) by which a displacement in the nanometre range can be detected and monitored. By use of two or three probes of this kind arranged at a short distance from the tissue of interest, the displacement of the tissue in a plane or in space can be monitored. Also known in the art and useful in the measurement of tissue position on a micrometer scale is laser triangulation and laser Doppler technology.

Laser Doppler instruments for precision measurements on microstructures being displaced a frequency of up to 20 MHz for use in the method and system of the invention are the MSV-050 Manual Microscope Adapter and the MSV-100 Remote Controlled Microscope Adapter of Polytec GmbH, Waldbronn, Germany. For displacement measurement on macrostructures their CLV-3D Compact 3-D Laser Vibrometer and PSV-400-3D Scanning Vibrometer can be used.

In studies of brain and spinal cord function of animals, confocal or multiphoton confocal microscopy can be used to monitor neuronal activity and neuronal structures. The effect of the beating heart and of respiration does however substantially reduce the resolution of images acquired by this kind of microscopy. Without stabilization finer details in the micrometer range of neurones, for instance synapses, may not be possible to visualize. By compensating for the periodical movement caused by the respiration and by the beating heart by the method and system of the invention these movements can be compensated to a considerable extent, and optical resolution correspondingly increased.

Another example for tissue stabilization in one, two or three dimensions according to the invention are recordings of neuronal activity by ultra-fine electrode tips of a diameter of down to $<10^{-6}$ m; in this case the tissue of interest is exposed by surgery, the one or more microelectrodes are inserted into the nervous system by means of a micromanipulator attached to a rigid frame. Movements of the tissue relative to the microelectrode caused by the heart beat or respiration will introduce electrical noise and may even cause injuries to neurons so as to impair or prevent recordings from the affected neurons; this risk is eliminated or at least substantially reduced by the method of the invention.

Position detectors are preferably disposed as close to the tissue of interest. The miniaturization of position detectors allows to follow even the movement of single nerve cells. The animal is placed on the base of an animal support table of the invention corresponding in principle to the patient support table of the embodiment in FIGS. 1 and 2, optionally fully or partially immobilized on the base in a desired position by an attachment means, such as fixation frame mounted at the top face of the base and in which the head or a portion of the spinal cord or a limb or other body part of the animal is placed and by which it is held. The displacement of a tissue of interest in the body part in question is compensated by electric or hydraulic actuators comprised by a positioning system of the invention. This arrangement allows the study of neuronal tissue by confocal or multiphoton confocal microscopy at conditions at which resolution of the image of the tissue is not or little impaired by the displacement the tissue due to muscular activity in the animal.

The invention claimed is:

1. A method for compensating a neurally triggered or other self-caused displacement of a tissue of an animal including man, comprised by a body part disposed, in a fixed relationship, on a base in contact with a displacement apparatus, the method comprising:
 (a) disposing an index marker in or in the proximity of the tissue or identifying, as an index marker, a structure in or in the proximity of the tissue;
 (b) sampling position data from said index marker or from said structure;
 (c) sampling source activity data from one or several sources of displacement;
 (d) correlating the position data and the source activity data to generate a predictive correspondence of the position data and the source activity data;
 (e) controlling the displacement apparatus in response to the predictive correspondence so as to displace the base in a manner compensating the predicted neurally triggered or other self-caused displacement of the tissue and thereby control the actual position of the body part tissue which has a fixed relationship with the base;

(f) updating the predictive correspondence in intervals or continuously.

2. The method of claim 1, comprising controlling the displacement apparatus in respect of acceleration and/or deceleration of the tissue by the displacement apparatus at the start or the end of a displacement.

3. The method of claim 1, wherein the compensatory displacement of the base is any of: linear, in a plane, in three-dimensional space.

4. The method of claim 1, wherein the base comprises an immobilization apparatus for holding said animal or person or a body part thereof in a fixed relationship to the base.

5. The method of claim 4, wherein the immobilization apparatus comprises a frame mounted on top of the base.

6. The method of claim 4, wherein the immobilization apparatus comprises a locking apparatus selected from clutch, ribbon, tape, adhesive pad or ribbon, and hook and eye straps.

7. The method of claim 5, comprising additionally displacing the frame in respect of the base by a displacement apparatus controlled by source activity data based on the predictive correspondence.

8. The method of claim 1, wherein the displacement apparatus is selected from hydraulic apparatus, solenoid apparatus, and electrical motor.

9. The method of claim 7, wherein the displacement apparatus effects displacement of the base and/or the frame in one direction and comprises a coarse displacement apparatus and a fine displacement apparatus.

10. The method of claim 9, comprising correcting a displacement of the base or the frame by said fine displacement apparatus based on feedback from a position sensor.

11. The method of claim 1, wherein the position data originates from an element selected from the group consisting of high speed video camera, laser Doppler shift detecting equipment, 3-D ultrasound apparatus, magnetic resonance apparatus, or X-ray apparatus.

12. The method of claim 1, wherein the index marker is selected from the group consisting of ink mark, coloured adhesive pad, metal implant, light emitting diode, and tissue structure.

13. The method of claim 1, where the source activity data comprises electromyographic (EMG) data from skeletal muscle and electrocardiogram (ECG) data.

14. The method of claim 1, in which the compensating displacement of the tissue is initiated by an electric signal from the source of the neurally triggered or other self-caused displacement.

15. The method of claim 1, wherein the correspondence is updated at intervals.

16. The method of claim 1, wherein the predictive correspondence is updated continuously.

17. A system for compensating a neurally triggered or other self-caused displacement of a tissue of an animal including man, comprising a base provided with an immobilizing apparatus for immobilizing the animal or person or body part thereof comprising said tissue, one or more displacement apparatuses in contact with the base, a first sampler for sampling position data from marker disposed in or in the proximity of the tissue, a second sampler for sampling source activity data from one or more sources of displacement, microprocessor for correlating position data and source activity data to generate a predictive correspondence of the position data and the source activity data, and a controller for controlling said one or more displacement apparatus in response to the predictive correspondence so as to displace the base in a manner compensating the predicted neurally triggered or other self-caused displacement of the tissue and thereby control the actual position of the body part tissue which is immobilized on the base.

18. The system of claim 17, comprising an updater for updating the predictive correspondence in intervals or continuously.

19. The system of claim 17, wherein the controller is responsive to acceleration and/or deceleration of said tissue by the displacement apparatuses at the start or the end of a displacement.

20. The system of claim 17, wherein the displacement apparatuses are capable of linear, planar, or three-dimensional displacement.

21. The system of claim 17, wherein the immobilization apparatus is mounted in a fixed or a displaceable relationship to the base.

22. The system of claim 21, wherein the immobilization apparatus comprises a frame provided with one or more locking apparatuses.

23. The system of claim 22, wherein the locking apparatuses are selected from the group consisting of clutch, ribbon, tape, adhesive pad or ribbon, and hook and eye straps.

24. The system of claim 17, wherein the displacement apparatuses are is selected the group consisting of from hydraulic apparatus, solenoid apparatus, and electrical motor.

25. The system of claim 17, wherein the displacement apparatuses comprises a coarse displacement apparatus and a fine displacement apparatus.

26. The system of claim 17, wherein the first sampler is selected from the group consisting of a high speed video camera, laser Doppler shift detecting equipment, 3-D ultrasound apparatus, magnetic resonance apparatus, and X-ray apparatus.

27. The system of claim 17, wherein the index marker is selected from the group consisting of ink mark, coloured adhesive pad, metal implant, light emitting diode, tissue structure, and bioresorbable radiation opaque material.

28. The system of claim 17, where the second sampler samples one or more of data selected from the group consisting of electromyographic (EMG) data from skeletal muscle, electrocardiogram (ECG) data, data from respiratory air flow, data from neuronal activity in the nervous system, or data related to smooth muscle activity.

29. The system of claim 17, wherein the displacement apparatuses comprise a drive for linear displacement of the base and comprises two or more sub-drives working in the same direction and/or in an opposite direction.

30. The system of claim 17, wherein the base is substantially flat and designed to be displaced in a plane corresponding to a horizontal face thereof.

31. The system of claim 30, wherein the base rests on a flat support and is disposable on the support in a horizontal plane.

* * * * *